(12) United States Patent
Xiao et al.

(10) Patent No.: US 8,906,205 B2
(45) Date of Patent: Dec. 9, 2014

(54) PROCESS FOR SEPARATING ETHYLENE GLYCOL AND 1,2-BUTANEDIOL

(71) Applicants: China Petroleum & Chemical Corporation, Beijing (CN); Shanghai Research Institute of Petrochemical Technology, SINOPEC, Shanghai (CN)

(72) Inventors: Jian Xiao, Shanghai (CN); Yanzi Guo, Shanghai (CN)

(73) Assignees: China Petroleum & Chemical Corporation, Beijing (CN); Shanghai Research Institute of Petrochemical Technology SINOPEC, Shanghai (CN)

( * ) Notice: Subject to any disclaimer, the term of this patent is extended or adjusted under 35 U.S.C. 154(b) by 184 days.

(21) Appl. No.: 13/736,893

(22) Filed: Jan. 8, 2013

(65) Prior Publication Data

US 2013/0284584 A1 Oct. 31, 2013

(30) Foreign Application Priority Data

Jan. 10, 2012 (CN) .......................... 2012 1 0005498

(51) Int. Cl.
*C07C 29/82* (2006.01)
*C07C 29/80* (2006.01)
*C07C 29/86* (2006.01)

(52) U.S. Cl.
CPC ................. *C07C 29/82* (2013.01); *C07C 29/80* (2013.01); *C07C 29/86* (2013.01)
USPC ................... 203/58; 203/50; 203/63; 203/64; 203/68; 568/852; 568/868

(58) Field of Classification Search
USPC ........... 203/50, 51, 56, 57, 58, 63, 64, 73, 74, 203/75, 78, 80, 81, 82, 84; 568/852, 868
See application file for complete search history.

(56) References Cited

U.S. PATENT DOCUMENTS

| 4,966,658 | A | | 10/1990 | Berg | |
|---|---|---|---|---|---|
| 5,645,695 | A | * | 7/1997 | Berg | ............................... 203/57 |
| 5,779,862 | A | * | 7/1998 | Berg | ............................... 203/57 |
| 6,299,737 | B1 | * | 10/2001 | Mohr et al. | ...................... 203/69 |
| 2012/0184783 | A1 | * | 7/2012 | Barnicki | ........................ 568/868 |

FOREIGN PATENT DOCUMENTS

CN 101928201 A 12/2010

* cited by examiner

*Primary Examiner* — Nina Bhat
*Assistant Examiner* — Brandi M Doyle
(74) *Attorney, Agent, or Firm* — Novick, Kim & Lee, PLLC; Allen Xue

(57) ABSTRACT

A process for separating ethylene glycol and 1,2-butanediol. A material flow containing ethylene glycol and 1,2-butanediol gets into the lower-middle part of the azeotropic rectification column C3 after the light components are removed by the separating columns C1 and C2, wherein the ethylene glycol and the azeotropic agent added from the top of the column form azeotrope which is distilled out from the top of the column and gets into the phase separator D1 after being condensed, the upper phase enriched with azeotropic agent after the phase was separated returns to the top of the column to continue to participate in azeotropy, and the lower phase enriched with ethylene glycol gets into the fourth separating column C4 to be refined to obtain the ethylene glycol product.

10 Claims, 1 Drawing Sheet

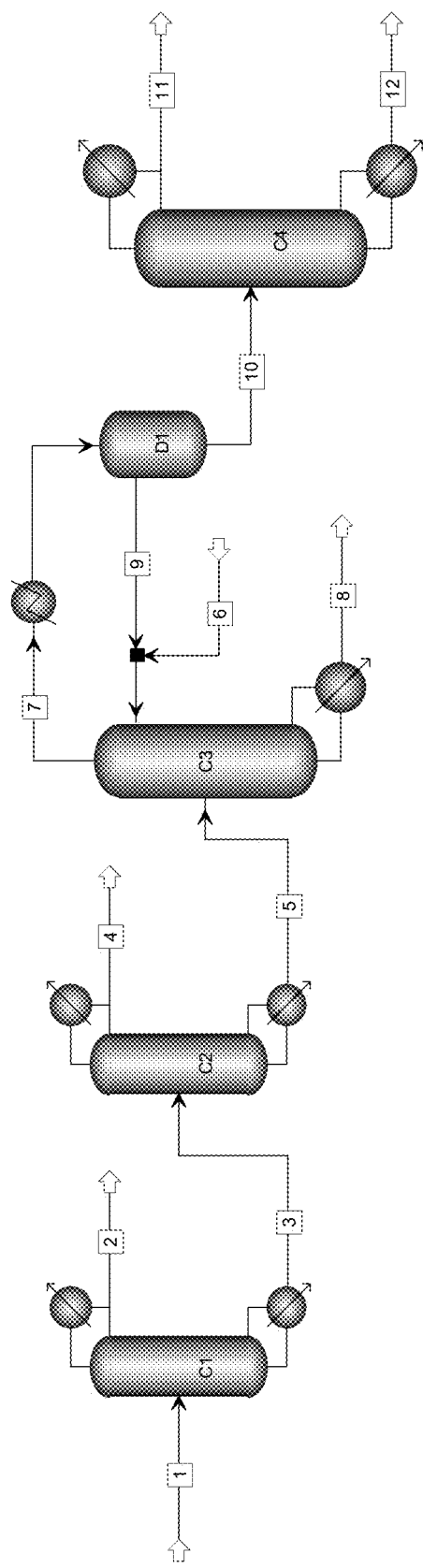

PROCESS FOR SEPARATING ETHYLENE GLYCOL AND 1,2-BUTANEDIOL

CROSS REFERENCE TO RELATED APPLICATION

The application claims priority to Chinese patent application No. 201210005498.1 filed on Jan. 10, 2012, which is hereby incorporated by reference herein in its entirety.

TECHNICAL FIELD

The present invention relates to a process for separating the mixture containing ethylene glycol and 1,2-butanediol, especially a process for separating and purifying ethylene glycol from the liquid phase product obtained by the hydrogenation of oxalate.

BACKGROUND OF THE INVENTION

Ethylene glycol is an important basic organic chemical material and is mainly used to copolymerize with terephthalic acid to produce polyethylene glycol terephthalate (PET). In addition, ethylene glycol can also be used to produce anti-freezing agent, lubricating agent, plasticizer, nonionic surfactant and explosive, etc, and it has a variety of uses. China is a big consumer of ethylene glycol. In recent years, with the constructions and operations of a number of large PET devices, the demands for ethylene glycol are increasing rapidly. Currently, the domestic output of ethylene glycol is far from being able to satisfy the demands. In 2010, China's import volume of ethylene glycol is 6.644 million tons, and it is estimated that by 2011, China's import volume of ethylene glycol will exceed 7 million tons. Hence, China's ethylene glycol industry has a good development prospect.

There are various process routes taking coal as the raw material to produce ethylene glycol, and one route having the best industrial prospect is to prepare oxalate through synthesis gas coupling and then produce ethylene glycol through the hydrogenation of oxalate. The reaction product obtained through the hydrogenation of oxalate to produce ethylene glycol comprises, in addition to the substances having lower boiling points such as methanol, glycollic acid ester, etc, a small amount of substances such as 1,2-propylene glycol and 1,2-butanediol which have the boiling points close to that of ethylene glycol and which can easily be subject to azeotropy with ethylene glycol and are hard to be separated through conventional rectification, wherein 1,2-butanediol has the boiling point closest to that of ethylene glycol and thus it is most difficult to separate 1,2-butanediol from ethylene glycol. Hence, the key of the problem is how to separate and remove 1,2-butanediol from ethylene glycol.

Besides, the route taking corn as raw material to produce ethylene glycol, 1,2-propylene glycol and 1,2-butanediol through biotransformation also draws the attention of various countries. To obtain various chemical alcohol products having high purities, including ethylene glycol and 1,2-butanediol, it still needs to solve the technical problem that conventional rectification requires many theoretical plates and large investment because the difference of the boiling points of ethylene glycol and 1,2-butanediol is too small.

There are few reports on the separation of ethylene glycol and 1,2-butanediol both at home and abroad. CN101928201 discloses purifying synthesis gas through the technical solution of saponification reaction, methanol-removal, hydrogenation reaction, three-column rectification and absorption treatment to prepare ethylene glycol crude product. The technical solution related in this patent does not separate 1,2-butanediol from ethylene glycol completely because 1,2-butanediol is subject to azeotropy with ethylene glycol during the process of separation and purification of three-column rectification. Moreover, it also causes product loss of ethylene glycol and reduces product yield. U.S. Pat. No. 4,966,658 discloses taking ethylbenzene, 3-heptanone and diisobutyl ketone, etc, as azeotropic agents to separate ethylene glycol and 1,2-butanediol or 1,3-butanediol by azeotropic rectification, and the number of theoretical plates of the rectification column is 30. However, the azeotropic agent related in this patent requires, during its use, a very high degree of vacuum (for example, 8 kPa) or a very long residence time (for example, 5-12 hours) in the case of lower degree of vacuum to obtain ethylene glycol with higher purity. And the content of ethylene glycol in the azeotrope at the top of the column is relatively lower, no more than 15%, and the resulting final product of ethylene glycol still contains about 100 ppm of 1,2-butanediol and a slight amount of azeotropic agents such as ethylbenzene, 3-heptanone and diisobutyl ketone, etc. Since these azeotropic agents have higher absorption in the optical ultraviolet region, the UV-transmittance of the product ethylene glycol is not high enough to meet the standard of superior grade product and thus said product is not suitable for industrial production.

SUMMARY

The technical problem to be solved in the present invention is to provide a new process for separating ethylene glycol and 1,2-butanediol from the mixture containing ethylene glycol and 1,2-butanediol in response to the problem in the prior art in separating ethylene glycol and 1,2-butanediol: the problem of large investment and high energy consumption caused by conventional rectification requiring a very high reflux ratio and a large number of theoretical plates as well as hard separation condition or unsatisfactory separation effects caused by conventional azeotropic agents when azeotropic rectification is applied. This new process has the advantages of small investment and low energy consumption as well as high purity and high UV-transmittance value of the resulting ethylene glycol product.

In order to solve the aforesaid technical problem, the technical solution that can be used by the present invention is as follows: a process for separating the mixture containing ethylene glycol and 1,2-butanediol, comprising distilling the mixture with the azeotropic agent having the following structural formula,

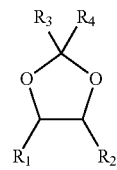

wherein $R_1$ is H atom or the alkyl containing 1-4 carbon atoms, preferably H atom or the alkyl containing 1-2 carbon atoms; $R_2$ is H atom or the alkyl containing 1-4 carbon atoms, preferably H atom or the alkyl containing 1-2 carbon atoms; $R_3$ is H atom or the alkyl containing 1-8 carbon atoms, preferably H atom or the alkyl containing 1-5 carbon atoms; $R_4$ is H atom or the alkyl containing 1-8 carbon atoms, preferably H atom or the alkyl containing 1-5 carbon atoms, making said material flow still for delaminating to separate out the mixture enriched with ethylene glycol, to obtain the material flow containing ethylene glycol and the azeotropic agent, and further distilling said mixture to obtain ethylene glycol. Preferably, the aforesaid distillation using azeotropic agent is carried out by using separating column, and preferably, the number of theoretical plates of said separating column is 8-30, the operating pressure is 30-101.3 kPa based on the absolute pressure, the reflux ratio R=0.8-5, and the mole ratio of azeotropic agent to ethylene glycol in the raw material is 0.1-10:1. Preferably, the content by weight percentage of the light components such as methanol, ethanol and glycollic acid ester in the raw material mixture containing ethylene glycol and 1,2-butanediol is less than 1%.

In one embodiment of the present invention, the present invention relates to a process for separating ethylene glycol and 1,2-butanediol from the mixture containing ethylene glycol and 1,2-butanediol, comprising the following steps:

a) optionally, material flow 1 of the mixture containing ethylene glycol and 1,2-butanediol gets into the lower-middle part of the first separating column C1, material flow 2 mainly comprising light components is distilled out from the top of the column, and material flow 3 mainly comprising ethylene glycol and 1,2-butanediol is discharged from the bottom of the column;

b) optionally, material flow 3 gets into the lower-middle part of the second separating column C2, material flow 4 mainly comprising light components is distilled out from the top of the column, and material flow 5 mainly comprising ethylene glycol and 1,2-butanediol is discharged from the bottom of the column;

c) material flow 5 gets into the lower-middle part of the third separating column C3, material flow 6 comprising said azeotropic agent is added from the top of the third separating column C3, material flow 7 of azeotrope formed mainly by the azeotropic agent and ethylene glycol is distilled out from the top of the column, and material flow 8 mainly comprising 1,2-butanediol is obtained at the bottom of the column;

d) after being condensed, material flow 7 gets into the phase separator D1 and is separated into the upper material flow 9 enriched with azeotropic agent and the lower material flow 10 enriched with ethylene glycol, and material flow 9 optionally returns to the top of the third separating column C3 to continue to participate in azeotropy;

e) material flow 10 gets into the upper-middle part of the fourth separating column C4, material flow 11 comprising azeotropic agent is distilled out from the top of the column, and the ethylene glycol product with the purity greater than 99.9% is obtained at the bottom of the column.

In one preferred embodiment of the aforesaid technical solution, the first separating column C1 is the first light component-removal column which mainly removes methanol in the raw material and has 10-30 theoretical plates; the operating pressure is atmospheric pressure; and the reflux ratio R=0.1-5. The second separating column C2 is the second light component-removal column which mainly removes ester compounds in the raw material and has 20-50 theoretical plates; the operating pressure is 40-101 kPa based on the absolute pressure; and the reflux ratio R=0.3-6. The third separating column C3 is azeotropic rectification column and has 8-30 theoretical plates; the operating pressure is 30-101.3 kPa based on the absolute pressure; and the reflux ratio R=0.8-5; the mole ratio of azeotropic agent to ethylene glycol in the raw material is 0.1-10:1, and azeotropic agent and ethylene glycol are immiscible. The fourth separating column C4 is ethylene glycol refining column and has 60-120 theoretical plates; the operating pressure is 10-101 kPa based on the absolute pressure; and the reflux ratio R=3-60. After refinement, the purity of ethylene glycol by weight percentage is no less than 99.9%, and the recovery rate of ethylene glycol is no less than 90%.

Since alcohol and aldehyde, ketone can be subject to condensation reaction with the action of protonic acid catalyst to form acetal and ketal compounds. These compounds are usually used as perfume materials and can also be used as special reaction solvents. The azeotropic agent provided in the present invention belongs to acetal and ketal compounds and can be synthesized by known aldol and hydroxyl keto condensation methods. For example, please see the following steps for reference: reactant I reacts with reactant II for 0.1-10 hours with the action of protonic acid catalyst III at the reaction temperature of 80° C.-250° C. and under the reaction pressure of 30-100 kPa based on the absolute pressure to get said azeotropic agent, wherein the mole ratio of reactant I to reactant II is 1-20:1, the concentration of catalyst III is 0.01-10% based on the mole percentage of the reaction mixture, and the structural formula of reactant I is as follows:

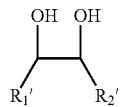

wherein $R_1'$ is H atom or the alkyl containing 1-4 carbon atoms, preferably H atom or the alkyl containing 1-2 carbon atoms; $R_2'$ is H atom or the alkyl containing 1-4 carbon atoms, preferably H atom or the alkyl containing 1-2 carbon atoms, and the structural formula of reactant II is as follows:

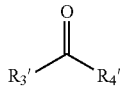

wherein $R_3'$ is H atom or the alkyl containing 1-8 carbon atoms, preferably H atom or the alkyl containing 1-5 carbon atoms; and $R_4'$ is H atom or the alkyl containing 1-8 carbon atoms, preferably H atom or the alkyl containing 1-5 carbon atoms. The molecule of reactant I preferably comprises 2-6 carbon atoms, and the molecule of reactant II preferably comprises 2-11 carbon atoms. The catalyst III is preferably selected from at least one of concentrated sulfuric acid, concentrated nitric acid, p-toluenesulfonic acid, phosphotungstic acid and acidic catalytic resin. The preferred range of the concentration of catalyst III is 0.05-5% based on the mole percentage of the reaction mixture.

The azeotropic agent used in the present invention has the characteristic of being able to form heterogeneous azeotrope having the lowest azeotropic temperature with ethylene glycol, and it can significantly increase the relative volatility of ethylene glycol and 1,2-butanediol to greatly reduce the number of theoretical plates and reflux ratio of the rectification column so as to achieve the effects of reducing investment and energy consumption. Since the azeotropic agent and ethylene glycol are not completely miscible, said azeotropic agent can, after forming azeotrope with ethylene glycol, be easily separated from ethylene glycol through simple separating operation and be recycled. Moreover, because ethylene glycol has a very low solubility in the azeotropic agent, the present invention reduces the loss of ethylene glycol and has higher work efficiency. The process of the present invention can be used to separate the material flow comprising ethylene glycol and 1,2-butanediol, including separating and purifying ethylene glycol from the liquid phase product obtained through the hydrogenation of oxalate as well as separating and purifying ethylene glycol and 1,2-butanediol from the production process of ethylene glycol taking corn as raw material. By using the process of the present invention, after refinement, ethylene glycol has the purity by weight percentage of no less than 99.9% and a recovery rate of no less than 90%. It can be seen that the process of the present invention achieves better technical effects.

BRIEF DESCRIPTION OF THE FIGURE

FIG. 1 illustrates an exemplary process flow chart of the present invention.

DETAILED DESCRIPTION

In FIG. 1, C1 is the first separating column (the first light component-removal column); C2 is the second separating column (the second light component-removal column); C3 is the third separating column (azeotropic rectification column); C4 is the fourth separating column (refining column); D1 is the phase separator. Material flow 1 is the material flow containing ethylene glycol and 1,2-butanediol; material flow 2 represents the light components with lower boiling points in material flow 1; material flow 3 is the material flow containing ethylene glycol and 1,2-butanediol after the light components with lower boiling points are removed from material flow 1; material flow 4 represents the light components with higher boiling points in material flow 1; material flow 5 is the material flow mainly containing ethylene glycol and 1,2-butanediol after the light components with higher boiling points are removed from material flow 3; material flow 6 is the fresh azeotropic agent; material flow 7 is the azeotrope formed by ethylene glycol and azeotropic agent; material flow 8 is the material flow which does not participate in azeotropy and which contains 1,2-butanediol and other components in material flow 1; material flow 9 is the phase separator upper material flow enriched with azeotropic agent; material flow 10 is the phase separator lower material flow enriched with ethylene glycol; material flow 11 represents a small amount of azeotropic agent and other compounds in material flow 10; material flow 12 is the final ethylene glycol product after the refinement of material flow 10.

According to the process flow as shown in FIG. 1, from material flow 1 containing ethylene glycol and 1,2-butanediol, material flow 2, i.e., the light components with lower boiling points is removed through the first separating column C1 and material flow 4, i.e., the light components with higher boiling points is removed through the second separating column C2, and then material flow 5 mainly containing ethylene glycol and 1,2-butanediol is obtained; in the third separating column C3, ethylene glycol in material flow 5 forms azeotrope 7 with the azeotropic agent in material flow 6 added from the top of the column, and said azeotrope 7 is distilled from the top of the third separating column C3 and gets into the phase separator D1 after being condensed; material flow 8 which mainly comprises 1,2-butanediol is obtained at the bottom of the column and can result in 1,2-butanediol product after being further refined; in the phase separator D1, the upper material flow 9 enriched with azeotropic agent returns to the top of the third separating column C3 to continue to participate in azeotropy, and the lower material flow 10 enriched with ethylene glycol gets into the fourth separating column C4 to be further refined, wherein after material flow 11 comprising azeotropic agent is distilled out from the top of the column, the ethylene glycol product with the purity of no less than 99.9% by weight is obtained at the bottom of the column.

EXAMPLES

The present invention will be further elaborated through the following examples.

Example 1

The process flow as shown in FIG. 1 was used. Material flow 1 was the liquid phase product obtained by the hydrogenation of oxalate and had the following components by weight percentage: methanol 85.65%, ethanol 0.20%, methyl glycolate 0.15%, dimethyl oxalate 0.45%, 1,2-propylene glycol 0.21%, 1,2-butanediol 0.40%, ethylene glycol 12.20%, diethylene glycol and other light and heavy components 0.84%.

The first separating column C1 was the first light component-removal column and had 20 theoretical plates, material flow 1 was introduced from the $15^{th}$ theoretical plate, the operating pressure was atmospheric pressure, the reflux ratio was 0.5, the temperature at the top of the column was 64.2° C., the temperature at the bottom of the column was 92.7° C., and the weight percentages of the components ethylene glycol and 1,2-butanediol in material flow 3 at the bottom of the column after 97% methanol was removed by the first light component-removal column C1 were: 73.2%, 0.61%.

The second separating column C2 was the second light component-removal column and had 50 theoretical plates, material flow 3 was introduced from the $35^{th}$ theoretical plate, the operating pressure was atmospheric pressure, the reflux ratio was 1.5, the temperature at the top of the column was 69.3° C., the temperature at the bottom of the column was 196.7° C., and the weight percentages of the components ethylene glycol and 1,2-butanediol in material flow 5 at the bottom of the column after the ester compounds having low boiling points such as methyl glycolate were removed by the second light component-removal column were: 94.54%, 0.79%.

The third separating column C3 was azeotropic rectification column and had 20 theoretical plates, material flow 5 was introduced from the $15^{th}$ theoretical plate, material flow 6 containing fresh azeotropic agent AZ1 (wherein the substituents $R_1, R_2, R_3$ and $R_4$ were —H, —H, —$CH_3$, —$(CH_2)_4CH_3$ respectively) was introduced from the top of the column, the mole ratio of azeotropic agent AZ1 to ethylene glycol in material flow 5 was 1.5:1, the operating pressure was atmospheric pressure, the reflux ratio was 2, the temperature at the top of the column was 166.7° C., the temperature at the bottom of the column was 200.5° C., azeotrope 7 formed by ethylene glycol and azeotropic agent was distilled out from the top of the column and got into the phase separator D1 after being condensed. After the phase was separated, the upper of D1 was material flow 9 enriched with azeotropic agent which returned to the top of the azeotropic rectification column to continue to participate in azeotropy, and the lower of D1 was material flow 10 enriched with ethylene glycol, namely, crude ethylene glycol product which did not contain 1,2-butanediol, and the weight percentage of ethylene glycol was 89.95%.

The fourth separating column C4 was ethylene glycol refining column and had 100 theoretical plates, material flow 10 was introduced from the $30^{th}$ theoretical plate, the operating pressure was 30 kPa based on the absolute pressure, the reflux ratio was 50, the temperature at the top of the column was 137.5° C., the temperature at the bottom of the column was 171.8° C., and after refinement, the ethylene glycol had a purity by weight percentage of 99.91% and a total recovery rate of 99.10%.

Example 2

The process flow as shown in FIG. 1 was used. Material flow 1 was the solution containing ethylene glycol and 1,2-butanediol and had the following components by weight percentage: methanol 29.46%, dimethyl oxalate 3.15%, 1,2-propylene glycol 1.18%, 1,2-butanediol 0.33%, ethylene glycol 65.09%, and other light and heavy components 0.79%.

The first separating column C1 had 10 theoretical plates, material flow 1 was introduced from the 8$^{th}$ theoretical plate, the operating pressure was atmospheric pressure, the reflux ratio was 0.3, the temperature at the top of the column was 64.2° C., the temperature at the bottom of the column was 192.5° C., and the weight percentages of the components ethylene glycol and 1,2-butanediol in material flow 3 after 95% methanol was removed by the first light component-removal column C1 were: 92.33%, 0.47%.

The second separating column C2 had 30 theoretical plates, material flow 3 was introduced from the 20$^{th}$ theoretical plate, the operating pressure was atmospheric pressure, the reflux ratio was 5, the temperature at the top of the column was 97.8° C., the temperature at the bottom of the column was 196.6° C., and the weight percentages of the components ethylene glycol and 1,2-butanediol in material flow 5 after the ester compounds having low boiling points such as methyl glycolate were removed by the second light component-removal column were: 96.59%, 0.51%.

The third separating column C3 was azeotropic rectification column and had 20 theoretical plates, material flow 5 was introduced from the 15$^{th}$ theoretical plate, material flow 6 containing fresh azeotropic agent AZ2 (wherein the substituents $R_1$, $R_2$, $R_3$ and $R_4$ were —$CH_3$, —$CH_3$, —$CH_2CH(CH_3)_2$, —$CH_2CH(CH_3)_2$ respectively) was introduced from the top of the column, the mole ratio of azeotropic agent AZ1 to ethylene glycol in material flow 5 was 0.5:1, the operating pressure was 50 kPa based on the absolute pressure, the reflux ratio was 3, the temperature at the top of the column was 156° C., the temperature at the bottom of the column was 185° C., azeotrope 7 formed by ethylene glycol and azeotropic agent was distilled out from the top of the column and got into the phase separator D1 after being condensed, the lower material flow 10 (namely, crude ethylene glycol product) after the phase was separated did not contain 1,2-butanediol, and the weight percentage of ethylene glycol was 89.65%. The fourth separating column C4 was ethylene glycol refining column and had 120 theoretical plates, material flow 10 was introduced from the 50$^{th}$ theoretical plate, the operating pressure was 30 kPa based on the absolute pressure, the reflux ratio was 40, the temperature at the top of the column was 136.8° C., the temperature at the bottom of the column was 171.8° C., and after refinement, the ethylene glycol had a purity by weight percentage of 99.95% and a total recovery rate of 93.15%.

Example 3

The process flow as shown in FIG. 1 was used. Material flow 1 was the solution containing ethylene glycol and 1,2-butanediol and had the following components by weight percentage: methanol 67.75%, ethanol 0.10%, dimethyl oxalate 0.5%, 1,2-propylene glycol 0.16%, 1,2-butanediol 0.45%, ethylene glycol 30.10%, and other light and heavy components 0.94%.

The first separating column C1 had 15 theoretical plates, material flow 1 was introduced from the 10$^{th}$ theoretical plate, the operating pressure was atmospheric pressure, the reflux ratio was 0.5, the temperature at the top of the column was 64.2° C., the temperature at the bottom of the column was 95.8° C., and the weight percentages of the components ethylene glycol and 1,2-butanediol in material flow 3 after 93% methanol was removed by the first light component-removal column C1 were: 81.76%, 1.23%.

The second separating column C2 had 40 theoretical plates, material flow 3 was introduced from the 30$^{th}$ theoretical plate, the operating pressure was 60 kPa based on the absolute pressure, the reflux ratio was 3, the temperature at the top of the column was 54.2° C., the temperature at the bottom of the column was 185.1° C., and the weight percentages of the components ethylene glycol and 1,2-butanediol in material flow 5 after the ester compounds having low boiling points such as methyl glycolate were removed by the second light component-removal column were: 97.74%, 1.47%.

The third separating column C3 was azeotropic rectification column and had 15 theoretical plates, material flow 5 was introduced from the 10$^{th}$ theoretical plate, material flow 6 containing fresh azeotropic agent AZ3 (wherein the substituents $R_1$, $R_2$, $R_3$ and $R_4$ were —H, —H, —$CH_2CH_3$, —$(CH_2)_2CH_3$ respectively) was introduced from the top of the column, the mole ratio of azeotropic agent AZ1 to ethylene glycol in material flow 5 was 3:1, the operating pressure was 30 kPa based on the absolute pressure, the reflux ratio was 5, the temperature at the top of the column was 136° C., the temperature at the bottom of the column was 162° C., azeotrope 7 formed by ethylene glycol and azeotropic agent was distilled out from the top of the column and got into the phase separator D1 after being condensed, the lower material flow 10 (namely, crude ethylene glycol product) after the phase was separated did not contain 1,2-butanediol, and the weight percentage of ethylene glycol was 88.33%.

The fourth separating column C4 was ethylene glycol refining column and had 100 theoretical plates, material flow 10 was introduced from the 50$^{th}$ theoretical plate, the operating pressure was 20 kPa based on the absolute pressure, the reflux ratio was 50, the temperature at the top of the column was 122.0° C., the temperature at the bottom of the column was 164.5° C., and after refinement, the ethylene glycol had a purity by weight percentage of 99.92% and a total recovery rate of 95.36%.

Example 4

The process flow as shown in FIG. 1 was used. Material flow 1 was the solution containing ethylene glycol and 1,2-butanediol and had the following components by weight percentage: methanol 52.75%, ethanol 0.05%, dimethyl oxalate 0.65%, 1,2-propylene glycol 0.53%, 1,2-butanediol 0.45%, ethylene glycol 45.03%, and other light and heavy components 0.59%.

The first separating column C1 had 15 theoretical plates, material flow 1 was introduced from the 10$^{th}$ theoretical plate, the operating pressure was atmospheric pressure, the reflux ratio was 0.3, the temperature at the top of the column was 64.2° C., the temperature at the bottom of the column was 167.8° C., and the weight percentages of the components ethylene glycol and 1,2-butanediol in material flow 3 after 96% methanol was removed by the first light component-removal column C1 were: 93.75%, 0.94%.

The second separating column C2 had 40 theoretical plates, material flow 3 was introduced from the 30$^{th}$ theoretical plate, the operating pressure was 80 kPa based on the absolute pressure, the reflux ratio was 5, the temperature at the top of the column was 85.3° C., the temperature at the bottom of the column was 191.3° C., and the weight percentages of the components ethylene glycol and 1,2-butanediol in material flow 5 after the ester compounds having low boiling points such as methyl glycolate were removed by the second light component-removal column were: 97.90%, 0.96%.

The third separating column C3 was azeotropic rectification column and had 30 theoretical plates, material flow 5 was introduced from the 20$^{th}$ theoretical plate, material flow 6 containing fresh azeotropic agent AZ4 (wherein the substituents $R_1$, $R_2$, $R_3$ and $R_4$ were —$CH_2CH_3$, —$CH_2CH_3$, —H, —$CH_3$ respectively) was introduced from the top of the column, the mole ratio of azeotropic agent AZ1 to ethylene glycol in material flow 5 was 2:1, the operating pressure was atmospheric pressure, the reflux ratio was 2, the temperature at the top of the column was 161° C., the temperature at the bottom of the column was 198° C., azeotrope 7 formed by ethylene glycol and azeotropic agent was distilled out from the top of the column and got into the phase separator D1 after being condensed, the lower material flow 10 (namely, crude ethylene glycol product) after the phase was separated did not contain 1,2-butanediol, and the weight percentage of ethylene glycol was 85.16%.

The fourth separating column C4 was ethylene glycol refining column and had 80 theoretical plates, material flow 10 was introduced from the 50$^{th}$ theoretical plate, the operating pressure was 15 kPa based on the absolute pressure, the reflux ratio was 60, the temperature at the top of the column was 112.8° C., the temperature at the bottom of the column was 160.0° C., and after refinement, the ethylene glycol had a purity by weight percentage of 99.92% and a total recovery rate of 92.81%.

Example 5

The mixture comprising the following components by weight percentage: methanol 0.23%, dimethyl oxalate 0.09%, 1,2-propylene glycol 0.79%, 1,2-butanediol 3.43%, ethylene glycol 95.32%, and other light and heavy components 0.14%, was taken as the raw material and was separated by the third separating column C3 and the fourth separating column C4 as shown in FIG. 1. The third separating column C3 was azeotropic rectification column and had 15 theoretical plates, the raw material was introduced from the 10$^{th}$ theoretical plate, material flow 6 containing fresh azeotropic agent AZ1 (wherein the substituents $R_1$, $R_2$, $R_3$ and $R_4$ were —H, —H, —$CH_3$, —$(CH_2)_4CH_3$ respectively) was introduced from the top of the column, the mole ratio of azeotropic agent AZ1 to ethylene glycol in the raw material was 1.5:1, the operating pressure was atmospheric pressure, the reflux ratio was 2, the temperature at the top of the column was 166.7° C., the temperature at the bottom of the column was 200.5° C., azeotrope 7 formed by ethylene glycol and azeotropic agent was distilled out from the top of the column and got into the phase separator D1 after being condensed. After the phase was separated, the upper of D1 was material flow 9 enriched with azeotropic agent which returned to the top of the azeotropic rectification column to continue to participate in azeotropy, the lower of D1 was material flow 10 enriched with ethylene glycol, namely, crude ethylene glycol product which did not contain 1,2-butanediol, and the weight percentage of ethylene glycol was 88.56%.

The fourth separating column C4 was ethylene glycol refining column and had 100 theoretical plates, material flow 10 was introduced from the 30$^{th}$ theoretical plate, the operating pressure was 25 kPa based on the absolute pressure, the reflux ratio was 60, the temperature at the top of the column was 130.3° C., the temperature at the bottom of the column was 168.4° C., and after refinement, the ethylene glycol had a purity by weight percentage of 99.96% and a total recovery rate of 98.30%.

Comparative Example 1

The liquid phase product obtained through the hydrogenation of oxalate in Example 1 was taken as raw material flow 1 and was separated by the process flow as shown in FIG. 1, wherein the operating conditions of the first separating column C1 and the second separating column C2 were the same as those in Example 1, no azeotropic agent was added to the third separating column C3 and the method of conventional rectification was used for separation, the other operating conditions were the same as those in Example 1, the temperature at the top of the column was 197.1° C. and the temperature at the bottom of the column was 225.8° C. The experimental results showed that the weight percentages of the components ethylene glycol and 1,2-butanediol in the distillate at the top of the third separating column C3 were 89.91% and 3.67%, which showed that ethylene glycol and 1,2-butanediol were not separated effectively; the distillate further got into the fourth separating column C4 for separation, wherein the number of theoretical plates of the separating column C4 was 120, the operating pressure was 25 kPa based on the absolute pressure, the reflux ratio was 130, the temperature at the top of the column was 140.0° C., the temperature at the bottom of the column was 168.0° C., and the ethylene glycol at the bottom of the column obtained after refinement had a purity by weight percentage of 99.04% and a total recovery rate of 49.56%.

Comparative Example 2

The liquid phase product obtained through the hydrogenation of oxalate in Example 1 was taken as raw material flow 1 and was separated by the process flow as shown in FIG. 1, wherein the operating conditions of the first separating column C1 and the second separating column C2 were the same as those in Example 1, ethylbenzene was added to the third separating column C3 as azeotropic agent and the mole ratio of ethylbenzene to ethylene glycol in material flow 5 was 3:1, the other operating conditions were the same as those in Example 1, the temperature at the top of the column was 132.0° C. and the temperature at the bottom of the column was 198.0° C. The experimental results showed: the azeotrope at the top of the third separating column C3 was added into the phase separator D1 after being condensed, the weight percentages of the components ethylene glycol and 1,2-butanediol in the lower material flow after the phase was separated were 94.35% and 2.64%, which showed that ethylene glycol and 1,2-butanediol were not separated effectively; the distillate further got into the fourth separating column C4 for separation, the operating conditions were the same as those in Comparative Example 1, the ethylene glycol at the bottom of the column obtained after refinement had the purity by weight percentage of 99.72% and the UV-transmittances were 78, 92 and 99 respectively when the wavelengths were 220 mm, 275 mm and 350 mm respectively, and after ethylene glycols which were obtained in Examples 1 and 2 were mixed, the UV-transmittances were 86, 95 and 100 respectively.

The invention claimed is:

1. A process for separating a mixture containing ethylene glycol and 1,2-butanediol, comprising:

distilling the mixture in presence of an azeotropic agent having the following general formula to obtain an azeotrope comprising ethylene glycol and the azeotropic agent,

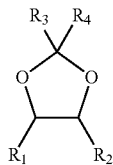

wherein $R_1$ is H atom or an alkyl containing 1-4 carbon atoms, $R_2$ is H atom or an alkyl containing 1-4 carbon atoms, $R_3$ is H atom or an alkyl containing 1-8 carbon atoms, and $R_4$ is H atom or an alkyl containing 1-8 carbon atoms;

separating the azeotrope to obtain a material stream enriched with ethylene glycol and a material stream enriched with the azeotropic agent; and distilling the material stream enriched with ethylene glycol to obtain ethylene glycol.

2. The process according to claim 1, wherein the azeotropic distillation is carried out in a separating column having 8-30 theoretical plates, wherein an operating pressure is 30-101.3 kPa based on absolute pressure, a reflux ratio is 0.8-5, and a molar ratio of the azeotropic agent to ethylene glycol is 0.1-10:1.

3. The process according to claim 1, wherein the content by weight percentage of light components in the mixture containing ethylene glycol and 1,2-butanediol is less than 1%.

4. A process for separating a mixture containing ethylene glycol and 1,2-butanediol, comprising the steps of:

a) optionally, feeding a material flow (1) of the mixture containing ethylene glycol and 1,2-butanediol into a lower-middle part of a first separating column (C1), obtaining a material flow (2) comprising light components from the top of the column, and a material flow (3) comprising ethylene glycol and 1,2-butanediol from the bottom of the column;

b) optionally, feeding the material flow (3) into a lower-middle part of a second separating column (C2), obtaining a material flow (4) comprising light components from the top of the column, and a material flow (5) comprising ethylene glycol and 1,2-butanediol from the bottom of the column;

c) feeding the material flow (1), the material flow (3), or the material flow (5) into a lower-middle part of a third separating column (C3), feeding a material flow (6) comprising an azeotropic agent into the top of the third separating column (C3), obtaining an azeotrope material flow (7) comprising the azeotropic agent and ethylene glycol from the top of the column, and material flow (8) comprising 1,2-butanediol from the bottom of the column;

d) feeding the material flow (7) into a phase separator (D1) and forming a material flow (9) enriched with the azeotropic agent and a material flow (10) enriched with ethylene glycol, and optionally returning the material flow (9) to the top of the third separating column (C3);

e) feeding the material flow (10) into an upper-middle part of a fourth separating column (C4), obtaining material flow (11) comprising the azeotropic agent from the top of the column, and an ethylene glycol product from the bottom of the column, wherein the ethylene glycol product has a purity of no less than 99.9% of ethylene glycol, wherein the azeotropic agent is of the following general formula

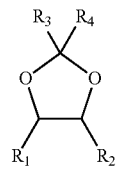

wherein $R_1$ is H atom or an alkyl containing 1-4 carbon atoms, $R_2$ is H atom or an alkyl containing 1-4 carbon atoms, $R_3$ is H atom or an alkyl containing 1-8 carbon atoms, and $R_4$ is H atom or an alkyl containing 1-8 carbon atoms.

5. The process according to claim 4, wherein the first separating column (C1) has 10-30 theoretical plates, an operating pressure at atmospheric pressure, and a reflux ratio R of 0.1-5.

6. The process according to claim 4, wherein the second separating column (C2) has 20-50 theoretical plates, an operating pressure of 40-101 kPa based on the absolute pressure, and a reflux ratio R of 0.3-6.

7. The process according to claim 4, wherein the third separating column (C3) has 8-30 theoretical plates, an operating pressure of 30-101.3 kPa based on the absolute pressure, and a reflux ratio R of 0.8-5, and a molar ratio of the azeotropic agent to ethylene glycol of 0.1-10:1.

8. The process according to claim 1, wherein the azeotropic agent and ethylene glycol are immiscible.

9. The process according to claim 4, wherein the fourth separating column (C4) has 60-120 theoretical plates, an operating pressure of 10-101 kPa based on the absolute pressure, and a reflux ratio R of 3-60.

10. The process according to claim 1, wherein $R_1$ is H atom or an alkyl containing 1-2 carbon atoms, $R_2$ is H atom or an alkyl containing 1-2 carbon atoms, $R_3$ is H atom or an alkyl containing 1-5 carbon atoms, and $R_4$ is H atom or an alkyl containing 1-5 carbon atoms.

* * * * *